United States Patent [19]

Shouval et al.

[11] Patent Number: 4,714,613

[45] Date of Patent: Dec. 22, 1987

[54] METHOD OF SUPPRESSING CELL GROWTH BY IMMUNOTHERAPY

[75] Inventors: Daniel Shouval, Jerusalem, Israel; David A. Shafritz, Larchmont, N.Y.; Jack R. Wands, Waban, Mass.

[73] Assignees: The Albert Einstein College of Medicine of Yeshiva University, New York, N.Y.; The General Hospital Corporation, Boston, Mass.

[21] Appl. No.: 428,653

[22] Filed: Sep. 30, 1982

[51] Int. Cl.$^4$ .................... A61K 39/42; A61K 39/00; C12P 21/00; C12Q 1/02

[52] U.S. Cl. ........................ 424/86; 424/85; 530/387; 530/388; 530/821; 530/828; 435/68; 435/29; 435/172.2

[58] Field of Search ............... 435/68, 240, 241, 948, 435/29, 172.2; 436/548; 260/112 R; 424/85, 86, 88, 89; 530/387, 388, 821, 828; 514/2, 8

[56] References Cited

U.S. PATENT DOCUMENTS

| | | | |
|---|---|---|---|
| 4,196,265 | 4/1980 | Koprowski et al. | 435/2 |
| 4,271,145 | 6/1981 | Wands et al. | 424/85 |
| 4,301,250 | 11/1981 | McAleer et al. | 435/241 |
| 4,361,549 | 11/1982 | Kung et al. | 424/85 |

OTHER PUBLICATIONS

Chakraburty et al., Nature vol. 286, p. 531, 1980.
Shouval et al., *Cancer Res.* vol. 41, p. 1312, 1981.
Nadler et al., *Cancer Res.* vol. 40, pp. 3147–3154, Sept. 1980.
Shouval et al., (including V. R. Zurawski and K. J. Isselbacher) *Hepatology* vol. 2, pp. 1285–1335, 1982.
Shouval et al., (including V. R. Zurawski, Jr.) *Hepatology* vol. 1, p. 542 (Abstract) Oct. 1, 1981.
Dulbecco et al., *Virology*, Dulbecco et al., eds., Harper & Row, 1980, pp. 1063–1066, 1125–1126, 1140–1145.
Zweig, M. et al., Journal of Virology, 32:676–678 (1979).
Pereira, L. et al., Proceedings of the National Academy of Sciences, USA, 78:5202–5206 (1981).
Goding, J., Journal of Immunological Methods, 39:285–308 (1980).
Fazekas de St. Groth, S. et al., Journal of Immunological Methods, 35:1–21 (1980).
Hybritech Sales Advertisement, effective Mar. 1, 1981.
Kennett, R. H., et al., (Editors), Monoclonal Antibodies–Hybridomas: A New Dimension in Biological Analyses (1980), pp. 363–419.
Fenner, F., in The Biology of Animal Viruses (1968), pp. 186, 649.
Young, W., Jr., et al., Science, 211:487–489 (1981).
Shouval, D. et al., Proceedings of the Natl. Academy of Sciences USA, 79:650–654 (1982).
Shouval, D. et al., Nature, 298:567–568 (1982).

*Primary Examiner*—Thomas G. Wiseman
*Assistant Examiner*—Robin Lyn Teskin
*Attorney, Agent, or Firm*—Saidman, Sterne, Kessler & Goldstein

[57] ABSTRACT

A selective method of suppressing the growth of cells which express a viral antigen on the surface thereof, which comprises administering to the cells a growth suppressing amount of a monoclonal antibody against said viral antigen, especially a method of suppressing the growth of hepatocytes or hepatoma cells persistently infected with HBsAg which comprises administering to the cells a growth suppressing or lethal amount of a complement fixing monoclonal IgM or IgG$_{2a}$ antibody against HBsAg.

6 Claims, 6 Drawing Figures

METHOD OF SUPPRESSING CELL GROWTH BY IMMUNOTHERAPY

BACKGROUND OF THE INVENTION

The work leading to the present invention was carried out in part under grants from the National Institutes of Health AM-17609, AM-17702, AA-02666, AM-20309, AG-04145, 1-KO2-AA-00048 and 3F05TW02764.

FIELD OF THE INVENTION

The present invention relates to an immunotherapeutic method for inhibiting growth of malignant or other cells infected with viruses.

DESCRIPTION OF THE PRIOR ART

In past years, there have been numerous attempts and manipulations proposed to control tumor growth by immunotherapy. These can be divided into passive and active immunotherapy categories (see for example Rosenberg, S. A. and Terry W. D., Advances in Cancer Research, 25:323 (1977)). Passive immunotherapy refers to approaches in which immunologic reagents such as serum, that are thought to have anti-tumor activity, are administered to a tumor-bearing host.

The ease of preparation and preservation of immune sera, as well as the development of increasingly sophisticated measures of antibody activity in the past 50 years have lead to many attempts to treat animal tumors with sera from immunized syngeneic, allogeneic or heterologous animals. In spite of many studies, however, the use of immune sera for the immunotherapy of malignant disease has been a relatively unrewarding area of investigation in cancer therapy.

Part of the difficulty may lie in the fact that the mechanism(s) for cell death or prevention of cell growth after introduction of antibodies is not completely understood and various possibilities exist. Antibodies directed against antigens in tumor cells may lead to cell lysis by both complement-mediated as well as antibodydependent lymphocyte toxicity. Soluble factors present in serum may be capable of "arming" non-committed lymphoid cells that, in turn, can react against the tumor cell. However, few studies of the passive immunotherapy of animal tumors with sera have attempted to dissect the mechanism of action for the observed effects.

In addition, there are a number of theoretical limitations concerning the potential usefulness of immunotherapy of tumors with immune serum. One of them is the limited accessibility of the extravascular space to cytotoxic IgM antibodies (because of their high molecular weight, e.g., 900,000 dalton) as a potential barrier to effective serotherapy against solid tumors (see for example Alexander, P., Cancer Research 27 2521-2526 (1967); and Hall et al Immunology 16:773-778 (1969)).

The recent advent of monoclonal antibody technology has brought a renewed interest in passive immunotherapy of tumors. For example Deng, C. et al in The Lancet, February 21, 1981 describe on page 403, the use of a monoclonal antibody against human leiomyosarcoma and suggest that it might be suitable for therapeutic trials. Herlyn, D. M. et al (Cancer Research 40:717-721 (1980)) describe the use of hybridoma- derived monoclonal anticolorectal carcinoma antibodies to suppress the growth of colorectal carcinoma cells in nude mice. Koprowski, H. et al (Proc. Nat. Acad. Sci. USA Vol. 75:3405-3409 (1978)) describe the use of monoclonal antibodies against a human melanoma. Bernstein, I. D., et al (Science 207:68-71 (1980)) describe the use of monoclonal antibodies against a thymus cell differentiation antigen as effective in therapy of transplanted mouse leukemia. Another passive immunotherapy treatment wherein the monoclonal antibody is directed against a tumor associated antigen is described by Nadler, L. M., et al (Cancer Research 40:3147-3154 (September 1980)). In this work, a monoclonal antibody directed against lymphoma-associated antigen was capable of mediating complement-dependent lysis, but not antibody-dependent cell-mediated cytotoxicity, in vitro against such lymphoma.

Of particular interest is the report of Young, W. W. and Hakomori S, Science, Vol. 211, 487-489 (1981), wherein a monoclonal antibody was prepared against a gangliotriosyl ceramide present in large quantities in mouse lymphoma L5178Y. Growth of the mouse lymphoma was suppressed by passive immunization with this monoclonal antibody, as long as the immunoglobulin was of the $IgG_3$ type but not of the IgM type, with or without added complement. These authors suggest that antibodies specific for tumor cell glycolipids can protect host animals against inoculated tumor cells. The particular ineffectiveness of IgM antibodies is discussed extensively in this work. The IgM antibody to the glycolipid is stated as causing only "marginal" increases in the survival time of mice, even though the antibody mediates complementdependent lysis of the lymphoma in vitro. The authors speculate that IgM may not readily diffuse into the tumor cells in vivo, or that the effectiveness of the $IgG_3$ antibody is due to an antibody-dependent cellular cytolytic mechanism.

In sum, this prior art indicates that previously, passive immunotherapy was a relatively ineffective area of cancer research, which is presently receiving renewed attention due to the availability of monoclonal antibodies. These antibodies have been prepared against whole cells, tumor-cell dependent antigens, or other antigens such as the glycolipid of Young and Hakomori, supra. It also appears reasonable to conclude that, in addition to the inherent difficulties of the method, there have been particular difficulties associated with the use of IgM monoclonal antibodies, and the art seems to shy away from or advise negatively for their use for passive immunotherapy.

In the present work, the inventors were interested in developing a method to combat or prevent the growth of hepatocellular carcinoma. As stated in Harrison's "Principles of Internal Medicine", 9th Ed., McGraw Hill Co., pages 1484-1486, carcinomas arising within the liver may be of liver cell (hepatocellular), bile duct cell (colangio cellular), or mixed cell origin. Hepatocellular carcinoma (primary liver cell carcinoma) accounts for 82 to 90% of liver carcinomas. There is wide variation in the incidence of hepatocellular carcinoma in different parts of the world, and a number of etiologic factors may be involved, among which viral hepatitis has been identified as one of the most important (Shafritz, D. A. and Kew, M. C., Hepatology, 1, 1-8, 1982). Viral hepatitis is endemic in many areas of the Mediterranean Basin, the Middle East, Africa and Asia. The prevalence of hepatitis B antigenemia in the normal population is 1 to 10% in these regions of the world and the majority of patients with hepatocellular carcinoma (which is usually superimposed on chronic liver disease), will also have serologic evidence of hepatitis B infection. Therefore, hepatitis B virus infection appears to be a significant causative factor in chronic liver disease, and subsequent development of primary liver cell carcinoma.

Recently, several human hepatoma cell lines in tissue culture have been developed from patients dying with hepatocellular carcinoma (e.g., SK-HEP-1, Mahlavu, CUSF and PLC/PRF/5). One of these human hepatoma cell lines, PLC/PRF/5, contains integrated hepatitis B virus DNA, and both synthesizes and secretes hepatitis B virus surface antigen (HBsAg; see for example Chakraborty, P. R., et al, Nature (London) 286:531 (1980) and Shouval, D., et al Cancer Research 41:1342 (1981)). When injected into Balb/c nude mice, these cells produce well vascularized and encapsulated tumors in almost 100% of animals within 10–21 days. It has also been demonstrated that HBsAg is present in the cytoplasm of greater than 50% of PLC/PRF/5 cells in culture or in PLC/PRF/5 solid tumors in nude mice. HBsAg was identified on the surface of up to 15% of cells in confluent cultures at any given time, using immunofluorescence techniques (Daemer, RJ, et al, in "Viral Hepatitis", The Franklin Institute Press, Philadelphia, 1978, p. 724; and Chisari, F. V. et al, Journal of Immunology 126:45 (1981)).

Because of the widespread occurrence of hepatitis infection in the world, and its relationship to hepatocellular carcinoma and other forms of liver disease such as chronic active hepatitis, a need exists for an efficient, selective method of treating chronic hepatitis B virus infection and its consequences.

In fact, a need continues to exist for an effective general technique which would be useful in passive immunotherapy, and which would provide more accurate and controllable results than those of the prior art.

SUMMARY OF THE INVENTION

It is therefore an object of the invention to provide a general method of passive immunotherapy.

It is another object of the invention to provide a method for the passive immunotherapy of virally infected cells.

Yet another object of the invention is to provide a method of immunotherapy for hepatocellular carcinoma.

These and other objects of the invention, as will hereinafter become readily apparent, have been attained by providing:

A method of suppressing the growth of cells which express a viral antigen on the surface thereof, which comprises administering to said cells a growth suppressing amount of a monoclonal antibody against said viral antigen.

In particular, other objects of the invention have been attained by providing:

A method of suppressing the growth of human hepatomas or hepatocytes persistently infected with hepatitis B virus and expressing hepatitis B surface antigen (HBsAg), which comprises administering to said cells a growth suppressing or cytolytic amount of a complement fixing monoclonal antibody against HBsAg.

BRIEF DESCRIPTION OF THE DRAWINGS

A more complete appreciation of the invention and many of the attendant advantages thereof will be readily obtained as the same become better understood by reference of the following detailed description, when considered in connection with the accompanying drawings, wherein.

DESCRIPTION OF THE PREFERRED EMBODIMENTS

Figure 1:
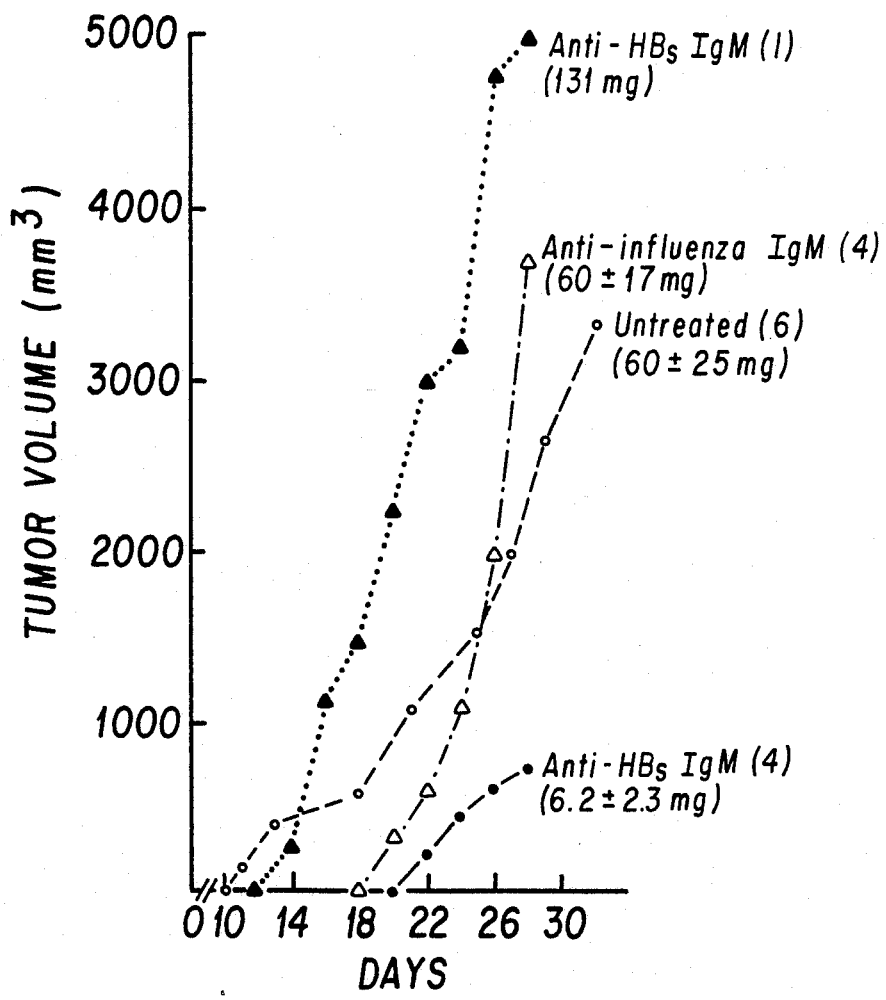
FIG. 1 shows the passive immunotherapy of PLC/PRF/5 human hepatoma growing in athymic nude (nu/nu) mice with monoclonal antibodies to hepatitis B surface antigen. The Figure demonstrates the time dependence of tumor volume on the nature of the monoclonal antibody administered. Anti-HBs IgM treated mice, suppressed tumors (●------●); anti-HBs IgM treated mice, non-responders (   --- ▲ ); anti-influenza HA protein treated mice (△- - - - △); untreated mice (○- - - - ○). (Numbers in parenthesis refer to animals in each group).

The present invention relates to a method of suppressing the growth of or destroying cells which express a viral antigen on the surface thereof, comprising administering to the cells a growth suppressing or lethal amount of a monoclonal antibody against the viral antigen.

The invention is based on the discovery that when a specific type of cell, namely a cell which expresses a foreign, viral antigen on its surface, is treated with an antibody against the viral antigen, the cell itself is destroyed. This discovery opens the door to a highly selective method of destroying such cells. Because the antibodies are specific for the foreign antigen i.e., an antigen not present in the cell or species when not infected, and the foreign antigen is expressed only on certain types of cells, the method permits the antibody to pinpoint with great accuracy the types of cells which are to be destroyed.

The method of the present invention avoids cross reactivity of the monoclonal antibodies with other cell type or components which are closely related to the antigen against which the monoclonal antibody is directed. Such cross reactivity has been, inter alia, one of the factors preventing the extensive use of passive immunotherapy for the treatment of tumors. This is because tumor antigens may not be unique or as clearly limited to tumor cells as was once thought, and may be expressed in other tissues and other cell types in the organism with proteins on their surface similar to the "tumor antigen", thus decreasing the overall selectivity of prior art passive immunotherapy treatments. This is particularly true for organs or tissues in an organism composed of rapidly dividing or germinal cells, such as gonadal tissue, mucosal cells and bone marrow stem cells, or cells of common ancestry or origin with the tumor cell during embryonal development. Under special circumstances, such as tissue regeneration, activation of cell growth or development, reexpression of antigens formerly thought to be specific for tumor cells may become manifest. Thus, the use of monoclonal antibodies directed against tumor cell surface specific antigens is problematic in terms of passive immunotherapy. This difficulty or limitation is avoided in the present invention because the antigen on the tumor cell surface toward which the monoclonal antibody is directed is never found in the organism except in those cells which are infected with the virus (e.g. hepatitis B virus) and are targeted for destruction.

In a more specific embodiment, the present invention relates to the suppression or stoppage of growth of tumor cells which express a viral antigen on its surface, more specifically that of hepatocellular carcinoma cells, which express the hepatitis B surface antigen.

The expression of the antigen may be permanent intermittant or transient, depending on the nature of the viral infection but must be present on the surface of the target cell at the time of therapy. The antibody must be capable of reaching the site on the cell surface of the cell where the antigen resides and interact with it. In the preferred embodiment, the viral antigen hepatitis B surface antigen can be demonstrated on the cell surface in a large proportion of infected hepatocytes or hepatocellular carcinoma cells, and therefore antibody uptake into the cell appears not to be a requirement.

For the present invention to be practiced the cells to be destroyed must be infected with the virus for which the monoclonal antibody is directed. By "infected" is meant that the cells must contain the genetic information of the virus (i.e. the viral DNA or RNA which codes for or directs the synthesis of the specific antigen in question). The cell need not contain the complete information of the virus nor express the complete virus particle, but only the protein against which the monoclonal antibody is directed. Thus, the cells could be infected with the complete virus or only a portion of the viral genetic information. The latter could be in the form of a naturally occurring virus or a chemically or biologically produced DNA element or vector (i.e. a recombinant plasmid, bacteriophage or other episomal element or a synthetic or mutated virus). Once the cell is infected with this material (naturally or artificially by transfection) and the viral antigen is produced, the invention can be practiced.

In cells which contain the appropriate viral information but are not persistently expressing the virus (latent), induction of viral antigen expression or complete virus replication may render the cells sensitive to monoclonal antibody immunotherapy. Latent cells may be induced to express viral proteins by the use of well known agents such as irradiation, chemical agents (IUDR or BUDR), steroids (e.g. prednisone), mutagens, chemotherapeutic agents and the like. The state of the viral genetic information in the cell (extrachromosomal in the form of virus particles or episomes or integrated into the host chromosomal DNA) is of importance only in that the status of the genetic information may influence expression of the specific viral antigen of interest.

There are a number of cells which persistently express foreign viral antigens, and which are included in the present invention. By the particular term "persistent" as used throughout this application, is meant to include any cells, whether in vivo or in vitro, whether part of a cell line or a tumor, which continuously and persistently produce and express a foreign antigen on the surface thereof.

In one of the embodiments, a persistently expressed viral antigen is one wherein the DNA of the viral antigen is integrated into the DNA of the genome of the host cell. Among these can be mentioned the hepatoma cell line PLC/PRF/5 and infected human hepatocytes in vivo (expressing HBsAg); Burkitt's lymphoma cells (expressing Epstein-Barr virus); acute and subacute inclusion body encephalitis such as subacute sclerosing panencephalitis (expressing herpes simplex and/or rubeola virus), or acute inclusion body encephalitis (expressing herpes simplex virus); multifocal panencephalopathy (expressing measles virus); cells from the brain or urogenital tract which express herpes type I, II or III virus, human T-cells infected with a lymphoma-leukemia virus (HTLV) and expressing specific lymphoma-leukemia virus protein(s), or any other cell which may express the antigenic determinants of a tumorigenic virus on the cell surface.

By the term "expression" used in the specification and claims, is meant that the viral antigen is produced by the host cell, due to its internal genetic mechanisms, and appears at an antibody-approachable site. In this sense, the antigen forms part of the outer antigenic composition of the cell surface. It needs to be transferred during or after synthesis from the inside of the cell to the outer surface thereof.

Any viral antigen which can be expressed in a host cell can be covered by the techniques of the present invention as long as the antibody can reach the site where the antigen resides and interacts with it to cause mortal injury. As stated previously, the DNA coding for the viral antigen may or may not be integrated into the genome DNA of the cell, and may be part of a plasmid, a mutant virus, a replicon, an episomal element, a recombinant DNA molecule and the like. Among the more common viral antigens covered in the present invention are herpes, hepatitis B surface antigen, measles, rubeola, vaccinia, Epstein-Barr virus and human T cell lymphomaleukemia virus.

The antibodies utilized in the present invention are human or non-human monoclonal antibodies against whole viruses or antigenic fragments thereof. The technique of obtaining monoclonal antibodies against viral antigens is well known and will not be described in detail any further, other than by reference to the following patents and publications, which are herein incorporated by reference. Koprowski et al describe continuous cell lines of genetically stable fused cell hybrids capable of producing large amounts of monoclonal antibodies against specific viruses. Koprowski et al, Proceedings of the National Academy of Sciences USA Vol. 74 p. 2985–2988, (1977) also describe somatic cell hybrids between mouse myeloma cells, and spleen cells which have been obtained from mice immunized with purified influenza virus. Wands et al U.S. Pat. No. 4,271,145 describe cell lines for producing monoclonal antibodies to hepatitis virus established by immunizing animal lymphocytes with hepatitis antigen, to form antibody-producing cells which are then fused with myeloma cells. These somatic cell hybrids can be cloned, and the clones produce monoclonal antibodies to individual antigenic determinants unique to the hepatitis virus. Wands et al in copending U.S. application Ser. No. 188,735 filed Sept. 19, 1980 for "Immunoassay Utilizing Monoclonal High Affinity IgM Antibodies," and which is herein also incorporated by reference, disclose monoclonal IgM antibodies useful for the immunoassay of viral antigens. Any of the cell lines described in these patents or publications useful to make monoclonal antibodies against viral antigens, and any of the monoclonal antibodies obtained therefrom can be used in the present invention. Of special interest are IgG antibodies obtained from cell line ATCC CRL-8017, IgM antibodies obtained from cell line ATCC CRL-8018 and antibodies from cell line ATCC HB-8058.

The antibodies used in the present invention may either be complement-fixing or non-complement fixing. If complement fixing, the antibodies interact with the cell surfaces and, upon complexation, cause the initiation of complement-dependent cell lysis. If non-complement fixing, the cell lysis may occur through antibody-dependent lymphocyte toxicity. Whether an antibody will be complement-fixing or non-complement-fixing is easy to determine by those skilled in the art. Thus, if cell lysis occurs even in the absence of complement, the monoclonal antibody is useful and is not a complement fixing antibody, and vice versa. Complement-fixing monoclonal antibodies are among the preferred monoclonal antibodies of the present invention.

In another embodiment, the monoclonal antibodies can be coupled to cytotoxic drugs, or substances that enhance cell killing, such as daunomycin, nitrogen mustards, cyclophosphamide, cobra venom factor, diphteria toxin, ricin, and the like.

An important and unexpected discovery of the present inventors is that complement-fixing monoclonal IgM antibodies can be used for cell lysis. This finding goes against the previous belief in the art that IgM antibodies could not be used for the passive immunotherapy of cancer cells. Rosenberg and Terry, supra, believed that IgM antibodies are not effective in therapy against solid tumors because they are inaccessible to the extravascular space. Young and Hakomori, supra had also found that passive immunization with monoclonal $IgG_3$ antibodies to glycolipids would inhibit growth of mouse lymphomas, but immunoglobulin M antibodies, with or without added complement, would not, and also explained that this effect could be due to a difficult diffusion of the IgM antibodies through the vascular space to the tumor cells in vivo. The present inventors, however, have discovered that IgM antibodies can be used successfully in immunotherapy. The reasons why such antibodies are effective in this regard may include inter alia, (1) high affinity for an antigen associated epitope ( e.g. Kasn for HBsAg is $4 \times 10^{11}$ liters/mole per molecule); and (2) multivalent attachment of the pentameric IgM to a multivalent antigen (e.g. HBsAg) on the cell surface.

The term "suppression" (as in growth suppression), used through the specification and claims, is meant to broadly include the prevention of cell growth, the blockage of further growth, the suppression of further growth, the slowing, stopping or inhibition of growth, and even the outright killing, e.g., via cell lysis, of cells that have already grown to a certain extent.

The techniques of the present invention can be applied for the suppression or destruction of cells both in vitro and in vivo. Of special interest is the application of the technique to the suppression of tumor growth, wherein the tumor cells persistently express a viral antigen, and wherein the suppression or regression of a solid tumor is caused by the immunotherapy of the present invention. Other, non-tumor conditions can also be treated. Among the typical conditions which may be treated according to the techniques of the present invention are the treatment of cells chronically infected with virus, such as HBsAg carrier hepatocytes, hepatocarcinomas, lymphomas, panencephalopathies, herpes virus infected cells and vaccinia infected cells and HTLV infected cells.

The monoclonal antibodies are administered either intravenously, by transfusion, by perfusion, intraperitoneally, intramuscularly, subcutaneously, or the like. The most common means of administration is by transfusion or intravenous injection. In the case when the antibody treatment is to cell lines in vitro, simple physical contact of the antibody solution or suspension with the cell line culture will suffice to bring about the desired results, cell lysis or suppression of cell growth.

By "growth suppression amounts" as used in the specification and claims, it is meant to include any amount of monoclonal antibody which will suppress (as the term is broadly used in the present invention) the growth of the host cells. Thus, any amount which will prevent, block, or remit growth can be utilized. Commonly, the antibodies are administered in a standard physiologically compatible carrier, such as saline solution and the like, in a concentration of 1 mg/ml to 50 mg/ml, preferably 5 mg/ml to 25 mg/ml. The administration of such solutions to an animal can be carried out from 1 to 3 times per day or less frequently, depending on the mode of administration, the nature of the growth, the extent, the localization, the duration, concurrent treatment, counter indications, nature of the antibodies, and the like. Generally, administration will range from 1 mg/kg to 150 mg/kg, preferably 50 mg/kg to 100 mg/kg. All of these variables are within the skill of the average practitioner, and will not be discussed any further.

The present invention is applicable to the suppression of tumor growth in tumor-carrying animals, including humans of both sexes.

In a highly preferred embodiment of the present invention, the antibodies are monoclonal IgM antibodies of high affinity or avidity for viral epitopes expressed on the affected cell surface membrane or IgG antibodies with similar properties and of subclasses other than $IgG_1$ and the cells are hepatocellular carcinoma cells whose growth is being prevented by administration of the antibodies. The hepatocellular carcinoma cells express hepatitis B surface antigen on their surface, and the antibodies are monoclonal antibodies against said antigen. In this sense, the invention therefore opens the way for treatment of hepatomas, for which the hepatitis virus is an etiologic agent.

Having now generally described this invention, the same will become better understood by reference to the following specific examples, which are included herein for purposes of illustration only and are not intended to be limiting of the invention or of any embodiments thereof.

The athymic, hairless (nude nu/nu) Balb/C mouse has been used widely to define and study the growth properties of various foreign tumors from allogenic as well as syngeneic hosts including man, when cells derived from such tumors or tissue culture cells prepared therefrom are injected subcutaneously. Previously, the inventors and others had observed that PLC/PRF/5 human hepatocellular carcinoma cells which express HBsAg could be grown into solid tumors when $5-10 \times 10^6$ cells were injected subcutaneously into the flank region of Balb/C nude mice (Shouval, D. et al Cancer Research 41:1342 (1981)) The injection schedule, lag period, growth properties and expression of viral proteins including HBsAg was studied in detail in this publication, and indicated that the nude mouse host could serve as an excellent model to test the effect(s) of anti-HBs monoclonal antibodies on the growth properties of PLC/PRF/5 cells in a living organism.

EXAMPLE 1

Immunotherapy of Human Hepatoma Cell Line PLC/PRF/5

I. Introduction

In the present example, IgM monoclonal antibodies to HBsAg determinants are shown to prevent tumor formation in 65% of treated mice injected with PLC/PRF/5 human hepatoma cells, and $IgG_{2a}$ monoclonal anti-HBs suppresses or prevents tumor growth in 65% of treated mice injected with PLC/PRF/5 cells.

Results

For immunotherapy, ascites fluid from three mouse hybridoma clones was used. Monoclonal antibodies in these ascitic fluid preparations bind specifically to HBsAg determinants and to PLC/PRF/5 cells in culture (see Example 2). In preliminary experiments, 100–200 μl of affinity purified $^{125}$I-labelled monoclonal anti-HBs from the three subclones was injected into Balb/c nude mice i.p. or i.v. Significant levels of $^{125}$I-anti-HBs were detected in nude mouse serum for up to three days following a single i.v. injection of $1 \times 10^6$ cpm of $^{125}$I-anti-HBs. This was measured by radioimmunoassay using HBsAg coated beads (provided by Abbott Laboratories, N. Chicago, Illinois). Following i.v. injection of 100 μl $^{125}$I anti-HBs IgM every 48 hrs for 8 days, $^{125}$I anti-HBs was detected in nude mouse serum at dilutions greater than 1:100 and was present in serum 5 days after the last i.v. injection. Significant serum levels of $^{125}$I anti-HBs IgM were not detected after i.p. injection. Intraperitoneal injection of $^{125}$I anti-HBs $IgG_{2a}$, however, produced high levels of anti-HBs activity in serum, similar to those obtained after i.v. injection of anti-HBs IgM. This demonstrated that significant serum levels of monoclonal antibodies were obtained and sustained after i.v. administration of monoclonal anti-HBs IgM or i.p. administration of monoclonal anti-HBs $IgG_{2a}$.

For immunotherapy experiments, the effect of unfractionated pooled ascitic fluid containing hybridoma antibodies on production and growth of PLC/PRF/5 tumors in nude mice was measured. The concentration of anti-HBs in these preparations (mouse hybridoma ascitic fluid) was 5 mg/ml for the IgM clone, (derived from cell line H25D32B82E8) and 25 mg/ml for the $IgG_{2a}$ clone (derived from cell line A5C32D31B8) and 25 mg/ml for the $IgG_1$ clone (derived from cell line A2C61G92F8. In the first 3 experiments, 100 μl of anti-HBs IgM or IgG were administered i.v. or i.p., respectively, every 48 hrs. Nude mice tolerated repeated injection of ascitic fluid for up to 4 weeks (3% mortality). Mice received IgM anti-HBs i.v., or $IgG_{2a}$ or $IgG_1$ i.p. within one hour after the injection of PLC/PRF/5 cells and at repeated intervals thereafter for 27–32 days. Control mice received 100 μl of PBS i.v. or i.p. unless stated otherwise. Cummulative successful intravenous injections score was 86±2%.

Injection of $1 \times 10^7$ PLC/PRF/5 cells s.c. into the flank region of Balb/c nude mice produced tumors in 37/39 injected mice (Table 1).

TABLE 1*

| Monoclonal Antibody Treatment* | Effect on Tumor Development | | | | |
|---|---|---|---|---|---|
| | No. Mice | un-affected | sup-pressed | ab-sent | p |
| none | 39 | 37 | — | 2 | — |
| anti-HBs IgM (i.v.) | 23 | 4 | 4 | 15 | p < 0.001 |
| anti-HBs $IgG_{2a}$ (i.p.) | 26 | 8 | 10 | 8 | p < 0.01 |
| anti-HBs $IgG_1$ (i.p.) | 10 | 9 | — | 1 | NS |
| anti-HA protein IgM (i.v.) | 6 | 4 | — | 2 | NS |
| anti-tetanus toxin $IgG_1$–$IgG_{2b}$ (i.p.) | 10 | 7 | — | 3 | NS |

*Effect of monoclonal antibodies to hepatitis B surface antigen on tumorigenicity of PLC/PRF/5 cells in Balb/c nu/nu mice. All mice were injected with $10^7$ PLC/PRF/5 cells on day 0, and 100 μl monoclonal antibodies i.v. or i.p., where indicated, starting 1 hr after tumor cell injection. Three control groups consisted of mice either untreated, or injected with 100 μl monoclonal antibodies to influenza hemagluttinin (HA) protein, or to tetanus toxin (other well defined monoclonal antibodies prepared against proteins not related to hepatitis B virus). Mice were sacrificed within 28–33 days after tumor cell injection. Significance P was determined by comparing experimental mice to the untreated controls using the chi square test.

Injection of IgM-anti HBs (i.v.) showed a protective effect against establishment or growth of PLC/PRF/5 tumors in 19/23 injected mice. Amongst these animals, anti-HBs IgM prevented tumor formation in 15 mice and suppressed tumor growth in additional 4 mice (p<0.001). Administration of anti-HBs $IgG_{2a}$ (i.p.) showed a protective effect against PLC/PRF/5 tumors in 17/26 animals (p<0.01). The response was less pronounced than that in anti-HBs IgM treated mice, since tumor formation was prevented in only 8 mice, but was suppressed in an additional 9 animals.

The effect of injecting a noncomplement fixing monoclonal anti-HBs on tumorigenicity of PLC/PRF/5 cells in athymic nude mice was also determined. This $IgG_1$ monoclonal anti-HBs attached to PLC/PRF/5 cells in culture as effectively as $IgG_{2a}$ or IgM anti-HBs (Example 2), but in tumor prevention studies, $IgG_1$ anti-HBs had no apparent protective effect (Table 1).

These in vivo results correlate well with the in vitro studies (Example 2), in which $IgG_{2a}$ and IgM monoclonal anti-HBs cause specific lysis of PLC/PRF/5 cells in the presence of complement, whereas addition of antiHBs $IgG_1$ plus or minus complement does not produce specific cell lysis as determined by the release of $^{51}Cr$ from these cells. (Other tests of cell death or loss of viability, such a Trypan Blue dye exclusion can be used, but these are less definitive for cell death than $^{51}Cr$ release, although the latter may actually underestimate the degree or extent of cell lysis. Nonetheless, the $^{51}Cr$ release assay can be used to determine whether a substantial portion of cells in culture are lysed, mortally damaged or frankly killed after treatment with monoclonal antibodies or other agents.)

Controls

Figure 2:
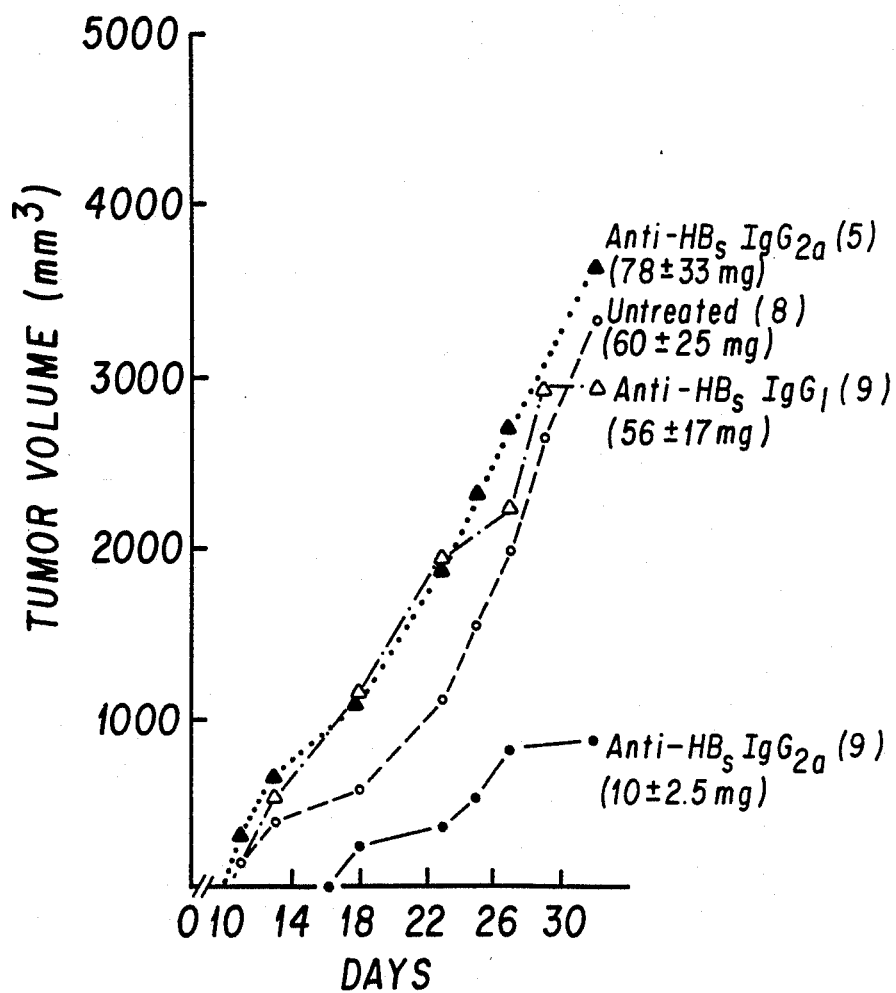
FIG. 2 shows the passive immunotherapy of PLC/PRF/5 human hepatoma growing in athymic nude (nu/nu) mice with monoclonal antibodies to hepatitis B surface antigen, demonstrating the time dependence of tumor volume for various antibodies. Anti-HBs IgG$_{2a}$ treated mice, suppressed tumors (●------●); anti-HBs IgG$_{2a}$ treated mice, non-responders (▲------▲); non-responder tumors in anti-HBs IgG$_1$ treated mice ( △------△ ); untreated mice (○------○). (Numbers in parenthesis refer to animals in each group).

To test whether ascitic fluid from hybridoma tumors or monoclonal antibodies against non-HBV determinants had a protective effect against PLC/PRF/5 cells (i.e. prevented and/or suppressed tumor growth), two additional groups of mice were injected with ascitic fluid containing monoclonal antibodies to non-HBV determinants. Monoclonal IgM antibodies to influenza HA protein (i.v.) or monoclonal antibodies to tetanus toxin (a mixture of $IgG_{2b}$ and $IgG_1$ subclasses given i.p.) produced little effect on PLC/PRF/5 tumor development (Table 1). Injection of PBS i.v. or i.p. had no effect on tumor growth in nude mice. Suppression of tumor growth by injection of monoclonal IgM or $IgG_{2a}$ anti-HBs was also evidenced by an increased latency from the day of tumor cell injection to the onset of gross tumor develoment, a slower tumor growth rate (measured by tumor volume), and a decreased tumor weight at necropsy as compared to untreated or other control animals. In four anti-HBs IgM treated mice with suppressed tumor growth, latency from tumor cell injection to tumor detection was prolonged to 20-22 days as compared to 11-13 days in control animals (FIG. 1). Latency was also prolonged to 16-18 days in the $IgG_{2a}$ anti-HBs treated group. Mean tumor volume was decreased in IgM and $IgG_{2a}$ treated mice with suppressed tumors, but was normal or increased in mice treated with monoclonal antibodies to non-HBV determinants (FIG. 2). No response was observed in $IgG_1$ anti-HBs treated mice. In animals with suppressed tumors (i.e. 4 anti-HBs IgM and 9 anti-HBs $IgG_{2a}$ treated animals), mean tumor weight was reduced by six to ten fold.

Interestingly, 1 mouse in the anti-HBs IgM treated group had a tumor more than twice as large as in control animals. Injection of $IgG_{2a}$ monoclonal anti-HBs did not produce a protective effect in 9/26 mice. In 5 of these animals, tumors were also larger than in control mice. With one exception when tumor was not palpable at termination of the experiment, tumor cells were not identified histologically at the tumor cell injection site. This provided evidence that the injected tumor cells were actually destroyed after certain monoclonal antibodies directed against HBsAg were introduced. The role of host immunity factors in the tumor cell destruction has not been clarified in these studies, but it is clear that under the conditions used (i.e. subcutaneous injection of $1 \times 10^7$ PLC/PRF/5 cells into the flank region of Balb/C athymic nude mice) gross tumors would have developed in nearly 100% of animals had these monoclonal antibodies not been given. In the $IgG_{2a}$ treated group in which tumor growth was suppressed, but not completely inhibited, large necrotic and hemorrhagic areas were observed throughout the tumor mass.

It has been shown that HBsAg levels in serum of nude mice injected with PLC/PRF/5 cells correlate with tumor weight (Shouval, D. et al Cancer Research 41:1342-1350 (1981)). Similar results were obtained in the present example (data not shown). In mice treated with all three monoclonal anti-HBs subclasses, (and independent of the effect of monoclonal anti-HBs treatment on tumor growth), free HBsAg in serum was not detected (Table 2).

TABLE 2*

| Monoclonal Antibody | No. Mice Treated | Effect on Tumor Growth | HBsAg and anti-HBs detection in serum ($^{125}I$ cpm, Mean ± S.E.) | |
|---|---|---|---|---|
| | | | HBsAg | anti-HBs |
| none | 8 | none | 9910 ± 1792 | 1692 ± 439 |
| anti-HBs IgM | 4 | suppression | 219 ± 25 | 29239 ± 414 |
| anti-HBs IgM | 7 | prevention | 207 ± 15 | 28816 ± 907 |
| anti-HBs IgM | 1 | enhancement (?) | 179 | 28144 |
| anti-HBs $IgG_{2a}$ | 5 | suppression | 580 ± 243 | 19178 ± 1375 |
| anti-HBs $IgG_{2a}$ | 3 | none or enhancement (?) | 360 ± 46 | 19893 ± 980 |
| anti-HBs $IgG_1$ | 9 | none | 232 ± 17 | 21368 ± 833 |
| anti-influenza HA Protein | 4 | none | 2794 ± 656 | 639 ± 62 |

*Detection of monoclonal antibodies to hepatitis B surface antigen (anti-HBs) and hepatitis B surface antigen (HBsAg) in PLC/PRF/5 tumor bearing Balb/c nu/nu mice. HBsAg and anti-HBs were determined at day of sacrifice using commercially available radioimmunoassay kits. Mice were sacrificed 28-32 days after tumor cell injection. All monoclonal anti-HBs treated mice had significantly lower concentration of HBsAg as compared to untreated controls ($P < 0.001$).

Anti-HBs levels in serum were still detectable at dilutions of 1:100 (Table 2), which suggests that sufficient anti-HBs was available to neutralize or complex with all HBsAg produced by the tumor cells. Even in tumor injected mice which did not respond to monoclonal anti-HBs treatment, HBsAg in the serum was completely neutralized.

Conclusions

The above studies show that injection of monoclonal antibodies to hepatitis B virus surface antigen determinants can specifically prevent or suppress the growth in nude mice of human hepatomas persistently infected with hepatitis B virus (HBV). This effect is unique in the sense that an antibody to a viral determinant rather than to a cellular protein can inhibit tumor growth. Although HBsAg was completely neutralized in the serum of all anti-HBs treated mice, HBsAg was identified in subcultures derived from tumors from 3 mice in which monoclonal antibody suppression was clearly evident, as well as in subcultures of 9 other treated and untreated animals. Therefore, the cells of these resistant or "escape" tumors still contained the genetic information for HBsAg synthesis and secretion, and were not subclones of tumor cells which had permanently lost this genetic capacity.

The dramatic effect of IgM anti-HBs treatment in preventing tumor formation may be due in part to large blood supply and access of the antibody to the tumor cells. The difference in effect of IgG$_{2a}$ versus IgM anti-HBs on tumor growth in nude mice is not clear, especially in view of the observation that both antibodies kill PLC/PRF/5 cells in vitro by complement mediated lysis (Example 2). Although IgG$_{2a}$ anti-HBs was injected in a 5 fold excess as compared to the IgM antiHBs, it had primarily a suppressive, but not a killing effect. Thus, mechanisms other than complement mediated lysis may be involved in tumor surveillance, as previously suggested in other systems. Although only limited data was available, it appeared in a small minority of cases that administration of monoclonal antiHBs enhanced rather than suppressed tumor growth. Such a phenomenon has been observed in prior art studies and the reason or reasons for its occurrence has not been adequately explained or understood.

EXAMPLE 2

IN VITRO STUDIES: SPECIFIC BINDING TO AND LYSIS OF HUMAN HEPATOMA CELL LINE PLC/PRF/5 BY MONOCLONAL ANTIBODIES TO HBsAg

Cell Culture Conditions

Three well-established human hepatoma cell lines PLC/PRF/5, SK-Hep 1 and Mahlavu were maintained in culture as monolayers in MEM supplemented with 10 mM nonessential amino acids, L-glutamine, penicillin and streptomycin (100 µl/ml), fungizone 2.5 µl/ml and 10% fetal bovine serum (complete medium). Cells were removed from subconfluent cultures with Trypsin-EDTA and counted.

The PLC/PRF/5 cells contain integrated HBV-DNA and both synthesize and secrete hepatitis B surface antigen (HBsAg). The SK-Hep 1 hepatoma cell line does not contain HBV-DNA and does not synthesize HBsAg. Under the conditions used, the Mahlavu cell line also does not synthesize HBsAg, although it was derived from an HBsAg carrier with primary hepatocellular carcinoma and is thought to contain very small amounts of HBV-DNA (less than 0.1 genome equivalent per cell).

Radioimmunoassays for Detection of Hepatitis B Markers

Solid phase radioimmunoassays (RIA) for detection of HBsAg or anti-HBs were performed on supernatants of cell cultures using commercial kits (Ausria® and Ausab®, Abbott Lab., N. Chicago, Il). A modified RIA for anti-HBs was used to determine biological activity of monoclonal antibodies to HBsAg. Two hundred µl of $^{125}$I-labelled monoclonal anti-HBs, IgM, IgG$_{2a}$ and IgG$_1$ subclasses, in various dilutions in 1% BSA and PBS was incubated for 12 hours at 37° C. with HBsAg coated beads (Abbott Laboratories, N. Chicago, Il). The beads were washed with 10 ml of distilled water and $^{125}$I anti-HBs bound to the beads determined with an LKB gamma counter (LKB Instruments, Inc., Rockville, MD).

Monoclonal Antibodies

Three cell hybrid clones with anti-HBs activity were tested for their ability to bind and/or lyse PLC/PRF/5 cells in culture. The following clones were utilized: (a) H$_{25}$D$_{32}$B$_{82}$E8, which produces ascitic fluid containing 5 mg/ml anti-HBs, IgM subtype; (b) A$_5$C$_{32}$D$_{31}$B8, which produces ascitic fluid containing 25 mg/ml anti-HBs, IgG$_{2a}$ subtype; and (c) A$_2$C$_6$1G2F8, which produces ascitic fluid containing 25 mg/ml anti-HBs, IgG$_1$ subtype. For all experiments either pooled sterile ascitic fluid or purified anti-HBs was used. For experiments with $^{125}$I-labelled antibodies, purified anti-HBs was used and iodination was performed using the Hunter-Bolton reagent. For some studies, monoclonal antibody to influenza HA protein (IgM subclass) was used, either in ascitic fluid or as purified $^{125}$I-labelled protein.

Binding of Monoclonal Anti-HBs to Hepatoma Cell Lines

To test whether monoclonal antibodies to HBsAg bind specifically to PLC/PRF/5 cells, $^{125}$I-labelled purified anti-HBs was added to hepatoma cells in culture 12–144 hours after seeding of the cells onto tissue culture plates. $2 \times 10^4$ trypsinized cells were plated in 96 microtiter flat bottom tissue culture plates (Flow Labs, McLean, VA), or in 24 well plates in 0.2 or 1 ml complete medium, respectively. For experiments of longer duration, medium was replaced every 48 hours. $1-2 \times 10^6$ cpm of $^{125}$I monoclonal anti-HBs or monoclonal antibody to influenza HA protein, suspended in complete medium, was added to cells in culture and incubated for 12 hours at 37° C. in 5% CO$_2$-95% air. All experiments were performed in triplicate and in twofold dilutions up to 1:2048 of the original $^{125}$I monoclonal antibody. After incubation, cells were washed gently 3 times with prewarmed complete medium and 0.2 ml of 1% SDS were added to each well. After an additional incubation for 4 hours at 37° C., total material in each well was collected and counted for $^{125}$I anti-HBs to PLC/PRF/5 cells. Competition experiments were performed by adding a 1000 fold excess unlabelled monoclonal anti-HBs to iodinated protein prior to incubation with PLC/PRF/5 cells. Simultaneously with each binding assay, the % of $^{125}$I monoclonal anti-HBs that bound specifically to HBsAg coated beads during a 12 hour incubation was also determined. Thus, for each dilution of $^{125}$I anti-HBs used, the maximal amount of iodinated protein which could bind to HBsAg on the surface of PLC/PRF/5 cells was measured. The percentage of "biologically active" anti-HBs was calculated as cpm bound to HBsAg coated beads versus total input of $^{125}$I cpm times 100.

Complement Mediated Lysis of PLC/PRF/5 Cells

To test whether monoclonal antibodies to HBsAg can specifically lyse PLC/PRF/5 cells in culture, a one stage complement lysis assay was performed. $5 \times 10^6$ trypsinized cells were washed once with complete medium and resuspended in 0.5 ml complete medium with 100 µ Ci Na$_2$$^{51}$CrO$_4$ (Amersham Searle Corp., Arlington Heights, Il). After incubation for 1 hour at 37° C. in 5% CO$_2$-95% air, cells were washed 3 times in complete medium. $2 \times 10^4$ viable cells in 200 µl complete medium were seeded into 96 well flat bottom tissue culture plates and incubated for 18 hours in 5% CO$_2$-95% air at 37° C. Cr$^{51}$ labelled cells were washed with prewarmed medium and incubated with ascitic fluid containing monoclonal antibodies to HBsAg or to non-HBV determinants at ten fold dilutions in the presence or absence of complement (1:12 dilution) in a final volume of 0.2 ml. After incubation, 0.1 ml of supernatant were collected and $^{51}$Cr released into the culture medium was measured using an LKB gamma counter. To each well with hepatoma cells, 0.1 ml of 1% SDS was added and plates were incubated overnight. 0.1 ml of each supernatant was again collected for determination of total radioactivity. Spontaneous or nonspecific $Cr^{51}$ release was taken as cpm $^{51}Cr$ released during incubation of target cells with complement in the absence of monoclonal anti-HBs. All determinations were performed at least in triplicate.

The spontaneous $Cr^{51}$ release for 1 hour incubation with medium alone, antibody alone or complement did not exceed 6, 8 and 14%, respectively. PLC/PRF/5 cells are extremely sensitive to complement as measured by $^{51}Cr$ release. Many batches of complement from various sources were screened and for most experiments, lyophilized low toxicity guinea pig complement (Cedarlane Lab., Hornby, Canada) at a dilution of 1:12 was used.

Results

HBsAg in the culture medium of PLC/PRF/5 cells is precipitated by monoclonal anti-HBs, IgM, $IgG_{2a}$ or $IgG_1$ subtypes and both cytoplasmic and cell surface membrane fluorescence for HBsAg can be demonstrated with this cell line. This indicates that PLC/PRF/5 cells produce and secrete HBsAg of human hepatitis B virus and that a portion of this viral antigen resides on the surface of these cells and the remainder resides in the cytoplasm. Addition of mouse hybridoma ascitic fluid containing monoclonal anti-HBs to PLC/PRF/5 cells in tissue culture did not affect attachment efficiency, growth rate or saturation density of these cells (data not shown).

$^{125}I$-labelled monoclonal anti-HBs, IgM, $IgG_{2a}$ and $IgG_1$ subtypes, bound specifically to PLC/PRF/5 cells in culture (Table 3).

TABLE 3

SPECIFICITY OF MONOCLONAL ANTIBODY BINDING TO HUMAN HEPATOMA CELLS IN VITRO

| Labelled monoclonal antibody | Excess unlabelled monoclonal antibody | Binding (mean cpm) to | |
|---|---|---|---|
| | | PLC/PRF/5 cells | SK-Hep 1 cells |
| anti-influenza HAP (IgM) | — | 10827 | 8958 |
| anti-HBs (IgM) | — | 48767 | 7227 |
| anti-HBs (IgM) | + | 9198 | — |
| anti-HBs ($IgG_{2a}$) | — | 29456 | 1012 |
| anti-HBs ($IgG_{2a}$) | + | 4526 | — |
| anti-HBs ($IgG_1$) | — | 57990 | 3421 |
| anti-HBs ($IgG_1$) | + | 14322 | — |

*Binding of monoclonal anti-HBs to human hepatoma cell lines. Two $\times 10^4$ cells were incubated with 1.25 $\times 10^6$ cpm (IgM) or 2.8 $\times 10^6$ cpm ($IgG_{2a}$ or $IgG_1$) monoclonal anti-HBs 48 hours after seeding for 12 hours at 37° C., 5% $CO_2$–95% air. Data represents binding of monoclonal antibodies to hepatoma cells as determined by detergent lysis of cells removed from the tissue culture plates and treated with 1% sodium dodecyl sulfate to solubilize the cells and release $^{125}I$-bound antibody.

For $2 \times 10^4$ cells, $^{125}I$-binding was dependent on the amount of anti-HBs added and ranged from $3-6 \times 10^4$ cpm with the various antibody preparations. This level of binding represented 2 ng of anti-HBs IgM per $2 \times 10^4$ cells or approximately $2.2 \times 10^4$ molecules per cell. Binding of monoclonal anti-HBs was 3–5 times greater than that observed with monoclonal anti-influenza HA protein labelled with $^{125}I$ to comparable specific activity. Binding of each $^{125}I$ anti-HBS was inhibited by addition of a 1000 fold excess of unlabelled anti-HBs of the same subtype and binding of all anti-HBs subtypes was substantially lower in SK-Hep 1 cells. The low level of $^{125}I$ anti-influenza HA protein binding observed in PLC/PRF/5 cells was also observed in SK-Hep 1 cells, which do not synthesize or secrete HBsAg.

Figure 3:
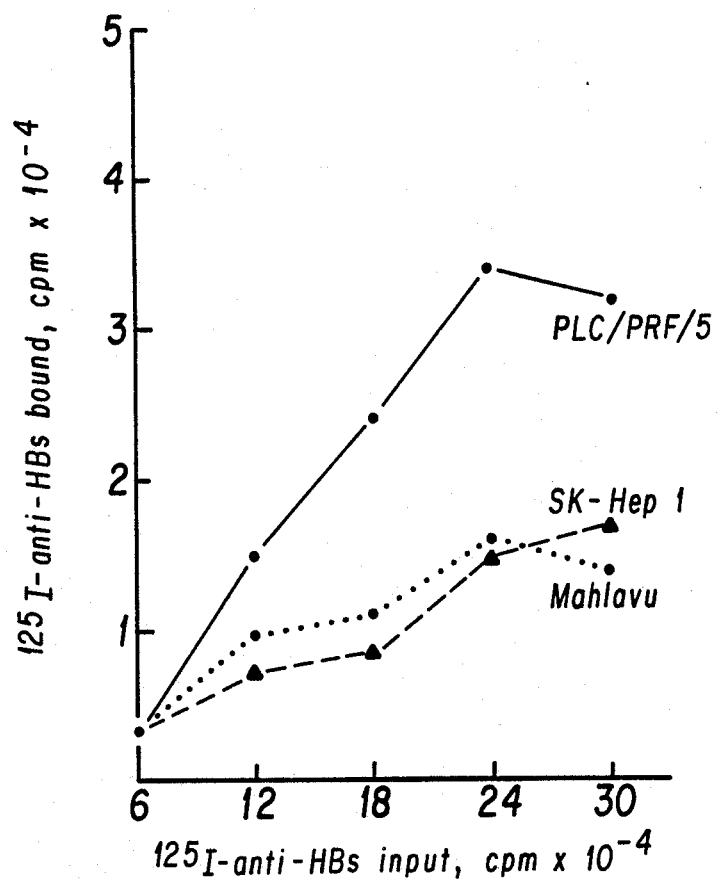
FIG. 3 demonstrates the binding of $^{125}$I anti-HBs to human hepatoma cell lines in vitro. The figure demonstrates the dependence of antibody binding to three different cell lines on the amount of antibody added. The cells lines shown are PLC/PRF/5 (●------●); SK-Hep 1 (▲ ------ ▲ ); and Mahlavu ( ■ ------ ■ ).
Figure 4:
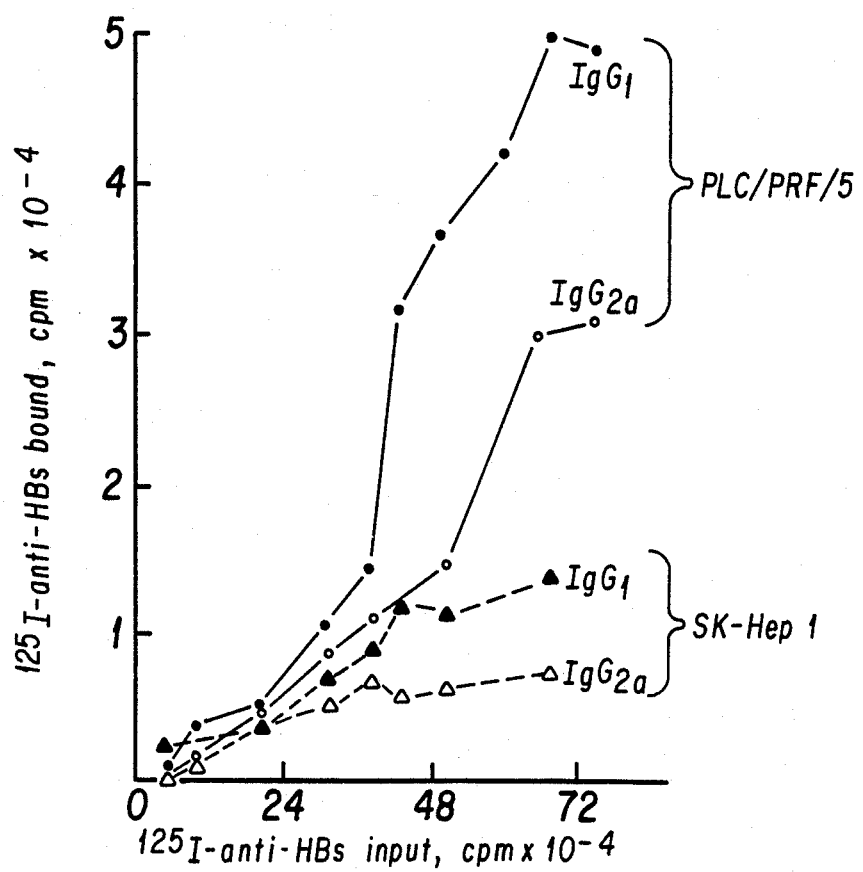
FIG. 4 shows the binding of $^{125}$I anti-HBs to human hepatoma cell lines in vitro, demonstrating the dependence of binding on the amount of antibody added. The legends are: anti-HBs A2C6(IgG$_1$) on PLC/PRF/5 cell line (●———●); anti-HBs A5C3(IgG$_{2a}$) on PLC/PRF/5 cell line (○———○); anti-HBs A2C-6(IgG$_1$) on cell line SK-Hep 1 ( ▲ ------ ▲ ); and anti-HBs A5C3(IgG$_{2a}$) on cell line SK-Hep Hep 1 ( △ ------ △ ).
Figure 5:
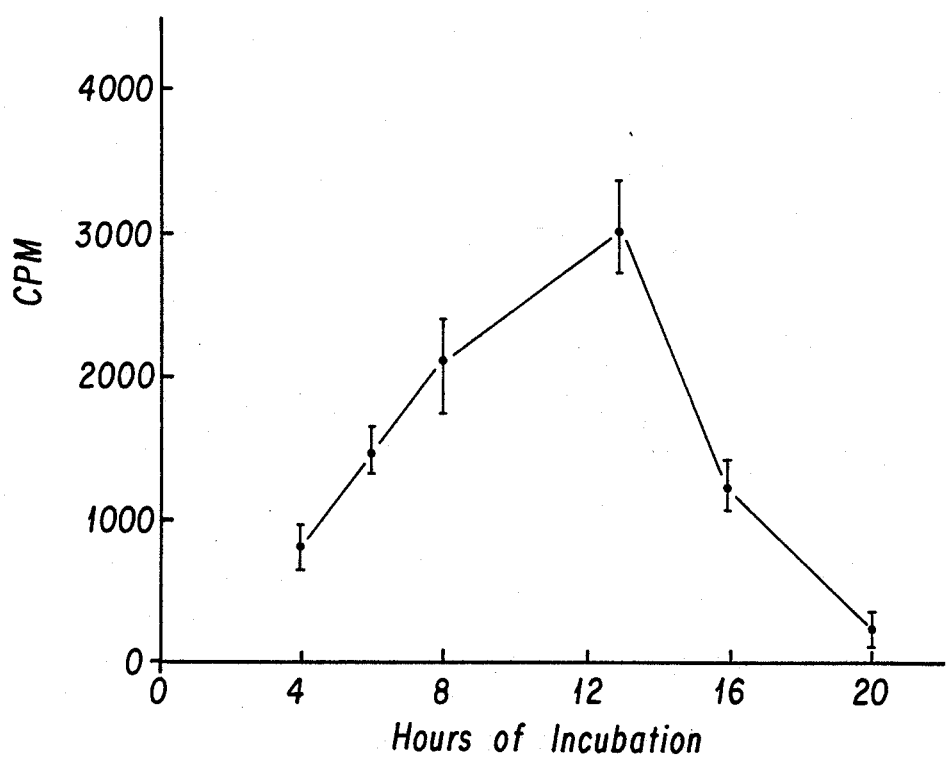
FIG. 5 shows the kinetics of binding of $^{125}$I antiHBs antibody 5D3 (IgM) binding to PLC/PRF/5 cells in vitro.

As shown in FIGS. 3 and 4, $^{125}I$ anti-HBs binding to PLC/PRF/5 cells was dependent on the amount of antibody added and reached a plateau at $3-6 \times 10^4$ cpm per $2 \times 10^4$ cells. For each preparation of $^{125}I$ anti-HBs, the amount of antibody capable of binding to HBsAg was determined by incubation of $^{125}I$ anti-HBs with HBsAg coated beads. This represented the maximum amount of material in the labelled antibody preparation which could bind to PLC/PRF/5 cells. For the experiments shown in FIGS. 3 and 4, when input of $^{125}I$ anti-HBs was corrected for the maximal amount of anti-HBs which could be bound to HBsAg, $^{125}I$ anti-HBs binding to PLC/PRF/5 cells reached plateau values at 14%, 4.2% amd 8.7% of input cpm for anti-HBs IgM, $IgG_{2a}$ and $IgG_1$, respectively. Binding of monoclonal anti-HBs (IgM subtype) was much lower with SK-Hep 1 or Mahlavu cells and was comparable to that obtained with anti-influenza HA protein IgM (c.f. FIG. 3 with Table 3). Binding of $^{125}I$ anti-HBs IgM to PLC/PRF/5 cells increased with time of incubation at 37° C. and reached a maximum at 12 hours (FIG. 5). More prolonged incubation of cells with $^{125}I$ anti-HBs led to a decrease in binding. Most binding assays were performed 48 hours after trypsinization and seeding of cells. However, incubations for 12–144 hours prior to addition of $^{125}I$ monoclonal anti-HBs did not affect binding significantly.

In order to determine whether monoclonal antibodies to HBsAg could specifically lyse PLC/PRF/5 cells in culture, cells were incubated with various antibodies in the presence or absence of complement. As shown in Table 4, both IgM and $IgG_{2a}$ monoclonal anti-HBs, but not $IgG_1$ monoclonal anti-HBs, lysed PLC/PRF/5 cells.

TABLE 4*

COMPLEMENT MEDIATED LYSIS OF PLC/PRC/5 CELLS BY MONOCLONAL ANTI-HBs

| Monoclonal Antibody | Complement 1:12 (g. pig) | lysis of PLC/PRF/5 cells** |
|---|---|---|
| — | + | 7.5 |
| anti-HBs (IgM) | — | 0 |
| anti-HBS (IgM) | + | 25.8 |
| anti-HBS (IgM) | + (heat inact.) | 1.1 |
| anti-HBS ($IgG_{2a}$) | — | 0 |
| anti-HBs ($IgG_{2a}$) | + | 26.7 |
| anti-HBs ($IgG_{2a}$) | + (heat inact.) | 0.1 |
| anti-HBs ($IgG_1$) | — | 2.4 |
| anti-HBs ($IgG_1$) | + | 9.9 |
| anti-influenza HA Protein | — | 0 |
| anti-influenza HA Protein | + | 8.8 |

*Monoclonal antibodies to HBsAg (anti-HBs) and to a non-HBV determinant (anti-influenza HA protein) were incubated with 2 $\times 10^4$ target cells/well 48 hours after seeding in flat bottom tissue culture plates in 200 μl of complete medium, with or without complement, for 1 hour at 37° C., 5% $CO_2$–95% air. Data are presented as % $^{51}Cr$ release (lysis).
**Data presented are corrected for $^{51}Cr$ release in the absence of complement or monoclonal antibodies which was 5.2%.

Figure 6:
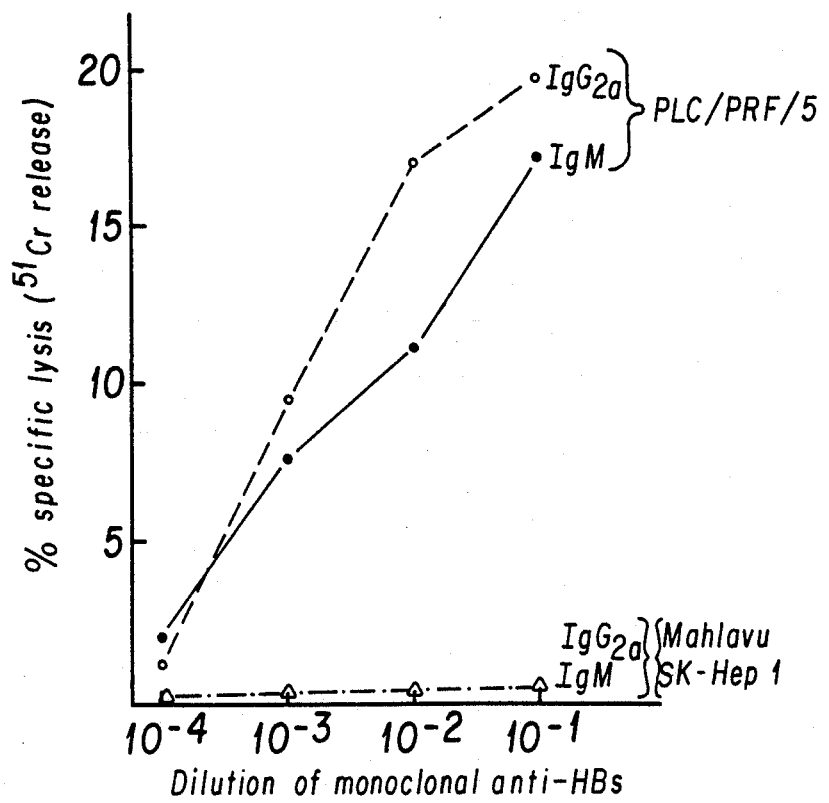
FIG. 6 shows the dependence of complement dependent lysis of various cell lines on the dilution of the monoclonal anti-HBs added to the culture medium for various antibodies: Anti-HBs IgG$_{2a}$ on cell line PLC/PRF/5 (○———○); anti-HBs IgM on cell line PLC/PRF/5 (●———●); anti-HBs IgM or IgG on Mahlavu cell line and on SK-Hep 1 cell line (△--.--.△); .

There was no specific lysis in the absence of complement, and heating complement to 56° for 30 minutes prior to its addition to PLC/PRF/5 cells prevented lysis. Rabbit and human complement gave essentially similar results. As shown in FIG. 6, the % specific lysis of PLC/PRF/5 cells was decreased with dilution of monoclonal anti-HBs added to the culture medium. Monoclonal anti-HBs did not cause specific lysis of SK-Hep 1 or Mahlavu cells in the presence of complement.

Having now fully described this invention, it will be readily apparent that the same can be performed within a wide and equivalent range of parameters, conditions, modes of administration, antibodies, and the like, without affecting the spirit or scope of the invention or any embodiment thereof.

What is claimed as new and is intended to be secured by Letters Patent is:

1. A method of selectively suppressing the growth of HBV infected hepatocytes or hepatoma cells which express or present, or which are capable of expressing or presenting HBsAg on the surface thereof, wherein said HBsAg is coded for by the DNA of the HBV, which comprises administering to said cells, while in the presence of other cells which do not express or present said HBsAg, a growth suppressing amount of a complement fixing monoclonal antibody against said HBsAg.

2. The method of claim 1 wherein said cells are PLC/PRF/5 cells.

3. The method of claim 1 wherein said antibody is an $IgG_{2a}$ antibody.

4. The method of claim 1 wherein said antibody is an IgM antibody.

5. The method of claim 1 wherein said cells are hepatoma cells present in a tumor in vivo.

6. A method of selectively suppressing the growth in vivo of HBV infected hepatocytes or hepatoma cells which express or present, or which are capable of expressing or presenting HBsAg on the surface thereof, wherein said HBsAg is coded for by the DNA of the HBV, which comprises administering to said cells, while in the presence of other cells which do not express or present said HBsAg, a growth suppressing amount of a complement fixing IgM monoclonal antibody against said HBsAg.

* * * * *